(12) United States Patent
Hon et al.

(10) Patent No.: US 8,463,554 B2
(45) Date of Patent: Jun. 11, 2013

(54) FINDING RELATIVES IN A DATABASE

(75) Inventors: Lawrence Hon, Millbrae, CA (US);
Serge Saxonov, San Mateo, CA (US);
Brian Thomas Naughton, Mountain View, CA (US); Joanna Louise Mountain, Menlo Park, CA (US); Anne Wojcicki, Palo Alto, CA (US); Linda Avey, Lafayette, CA (US)

(73) Assignee: 23andMe, Inc., Mountain View, CA (US)

( * ) Notice: Subject to any disclaimer, the term of this patent is extended or adjusted under 35 U.S.C. 154(b) by 506 days.

(21) Appl. No.: 12/644,791

(22) Filed: Dec. 22, 2009

(65) Prior Publication Data

US 2010/0223281 A1    Sep. 2, 2010

Related U.S. Application Data

(60) Provisional application No. 61/204,195, filed on Dec. 31, 2008.

(51) Int. Cl.
*G06F 7/00*    (2006.01)
(52) U.S. Cl.
USPC .................. 702/19; 702/20; 703/11; 707/700
(58) Field of Classification Search
None
See application file for complete search history.

(56) References Cited

U.S. PATENT DOCUMENTS

| | | |
|---|---|---|
| 2003/0203370 A1 | 10/2003 | Yakhini et al. |
| 2005/0064476 A1 | 3/2005 | Huang et al. |
| 2005/0191731 A1 | 9/2005 | Judson et al. |
| 2007/0037182 A1 | 2/2007 | Gaskin et al. |
| 2008/0154566 A1 | 6/2008 | Myres et al. |
| 2008/0189047 A1 | 8/2008 | Wong et al. |

OTHER PUBLICATIONS (Zhao and Liang, 2001, Journal of Computational Biology, vol. 8 No. 2 pp. 191-200.*
Blackwell et al. Proceedings / . . . International Conference on Intelligent Systems for Molecular Biology ; ISMB. International Conference on Intelligent Systems for Molecular Biology, (1999) pp. 54-59.*
Chen, M. et. al. American Journal of Human Genetics, Nov. 2007; vol. 81, No. 5, pp. 913-926.*
Ning et al., "SSAHA: A Fast Search Method for Large DNA Databases", Genome Research, Oct. 2001; vol. 11, No. 10, pp. 1725-1729.

* cited by examiner

*Primary Examiner* — Mary Zeman
(74) *Attorney, Agent, or Firm* — Van Pelt, Yi & James LLP

(57) ABSTRACT

Determining relative relationship includes receiving recombinable deoxyribonucleic acid (DNA) information of a first user and recombinable DNA information of a second user, determining, based at least in part on the recombinable DNA information of the first user and recombinable DNA information of the second user, a predicted degree of relationship between the first user and the second user, and in the event that the expected degree of relationship between the first user and the second user at least meets the threshold, notifying at least the first user about a relative relationship with the second user.

39 Claims, 15 Drawing Sheets

| LIST VIEW | DISCOVERY VIEW | | | | |
|---|---|---|---|---|---|
| FILTER PREDICTED RELATIVES: | ALL RESULTS (0) ▼ | | | | NO RESULTS |
| CONTACT STATUS | PREDICTED RELATIONSHIP | RELATIONSHIP RANGE | PERSONAL DETAILS | % DNA SHARED | # SHARED SEGMENTS |
| | | SHOW CLOSE RELATIVES | | | |

FIG. 4A

| LIST VIEW | DISCOVERY VIEW | |
|---|---|---|
| FILTER PREDICTED | | NO RESULTS |
| CONTACT STATUS | | % DNA SHARED # SHARED SEGMENTS |

ABOUT VIEWING CLOSE RELATIVES ⊠

IN RELATIVE FINDER, A CLOSE RELATIVE IS A PERSON WHO SHARES ENOUGH DNA WITH YOU TO BE AT LEAST AS CLOSELY RELATED AS A FIRST COUSIN. IF YOU'RE ALREADY GENOME SHARING WITH A CLOSE RELATIVE. THEY WILL AUTOMATICALLY APPEAR IN YOUR RESULTS. OTHERWISE, YOUR CLOSE RELATIVES WILL NOT APPEAR IN YOUR RESULTS UNLESS THEY'VE ALSO CHOSEN TO VIEW CLOSE RELATIVES.

KEEP IN MIND...

THERE IS A CHANCE THAT YOU MIGHT FIND OUT ABOUT CLOSE RELATIVES THAT YOU DIDN'T KNOW YOU HAD. FOR SOME PEOPLE, THIS COULD BE WELCOME NEWS. FOR OTHERS, THIS COULD BE SURPRISING OR UNCOMFORTABLE INFORMATION.

[CONTINUE TO CLOSE RELATIVES] [CANCEL]

FOR MORE ABOUT
✉ SEND FEEDB

FIG. 4B

| LIST VIEW | DISCOVERY VIEW | | | | |
|---|---|---|---|---|---|
| FILTER PREDICTED RELATIVES: | ALL RESULTS (12) | | | colspan="2" | RESULTS 1-10 OF 12 |
| CONTACT STATUS | PREDICTED RELATIONSHIP | RELATIONSHIP RANGE | PERSONAL DETAILS | % DNA SHARED | # SHARED SEGMENTS |
| MAKE CONTACT | 4TH COUSIN | 4TH TO 10TH COUSIN | FEMALE MATERNAL HAPLOGROUP F3 | 0.19% | 2 |
| MAKE CONTACT | 5TH COUSIN | 3RD TO 10TH COUSIN | FEMALE CENTRAL ASIAN ANCESTRY MATERNAL HAPLOGROUP G | 0.12% | 1 |
| MAKE CONTACT | 5TH COUSIN | 3RD TO 10TH COUSIN | MALE MATERNAL HAPLOGROUP G1A PATERNAL HAPLOGROUP B1b1b2a1a2d | 0.11% | 1 |
| MAKE CONTACT | 5TH COUSIN | 4TH TO 10TH COUSIN | MALE MATERNAL HAPLOGROUP R9b PATERNAL HAPLOGROUP O3a3c | 0.10% | 1 |
| MAKE CONTACT | 5TH COUSIN | 4TH TO 10TH COUSIN | FEMALE MATERNAL HAPLOGROUP B | 0.09% | 1 |
| MAKE CONTACT | 5TH COUSIN | 4TH TO 10TH COUSIN | MALE MATERNAL HAPLOGROUP D4C1 PATERNAL HAPLOGROUP O3a | 0.09% | 1 |
| MAKE CONTACT | 5TH COUSIN | 4TH TO 10TH COUSIN | MALE MATERNAL HAPLOGROUP F1a1* PATERNAL HAPLOGROUP O1a1* | 0.09% | 1 |
| SHARING GENOMES SEND A MESSAGE | PARENT OR CHILD | - | ****** MATERNAL HAPLOGROUP C | 50.11% | 24 |

FIG. 4C

| CONTACT STATUS | PREDICTED RELATIONSHIP | RELATIONSHIP RANGE | PERSONAL DETAILS | % DNA SHARED | # SHARED SEGMENTS |
|---|---|---|---|---|---|
| THIS PERSON WOULD LIKE TO CONTACT YOU. VIEW MESSAGE | AUNT/UNCLE NEPHEW, NIECE OR HALF-SLIBLING | - | DANIEL LAWRENCE RF2_, MATERNAL HAPLOGROUP U5a1* PATERNAL HAPLOGROUP R1b1b2a1a2d3* | 20.22% | 43 |
| CONTACT ACCEPTED SEND A MESSAGE VIEW CONVERSATION | SIBLING | - | ERIN LAWRENCE RF2_, MATERNAL HAPLOGROUP H1 | 46.75% | 29 |

FIG. 4H

```
Alice   A G T | C T G | C A A | ... -- 902
        C G A | C A G | T C A | ... -- 904

Bob     C A T | G A C | C C G | ... -- 906
        A A T | C T G | C A A | ... -- 908
```

FIG. 9

FINDING RELATIVES IN A DATABASE

CROSS REFERENCE TO OTHER APPLICATIONS

This application claims priority to U.S. Provisional Patent Application No. 61/204,195 entitled FINDING RELATIVES IN A DATABASE OF USERS filed Dec. 31, 2008 which is incorporated herein by reference for all purposes.

BACKGROUND OF THE INVENTION

Genealogy is the study of the history of families and the line of descent from ancestors. It is an interesting subject studied by many professionals as well as hobbyists. Traditional genealogical study techniques typically involve constructing family trees based on surnames and historical records. As gene sequencing technology becomes more accessible, there has been growing interest in genetic ancestry testing in recent years.

Existing genetic ancestry testing techniques are typically based on deoxyribonucleic acid (DNA) information of the Y chromosome (Y-DNA) or DNA information of the mitochondria (mtDNA). Aside from a small amount of mutation, the Y-DNA is passed down unchanged from father to son and therefore is useful for testing patrilineal ancestry of a man. The mtDNA is passed down mostly unchanged from mother to children and therefore is useful for testing a person's matrilineal ancestry. These techniques are found to be effective for identifying individuals that are related many generations ago (e.g., 10 generations or more), but are typically less effective for identifying closer relationships. Further, many relationships that are not strictly patrilineal or matrilineal cannot be easily detected by the existing techniques.

BRIEF DESCRIPTION OF THE DRAWINGS

Various embodiments of the invention are disclosed in the following detailed description and the accompanying drawings.

FIGS. 4A-4I are screenshots illustrating user interface examples in connection with process 300.

FIG. 9 is a diagram illustrating an example in which phased data is compared to identify IBD.

DETAILED DESCRIPTION

Figure 1:
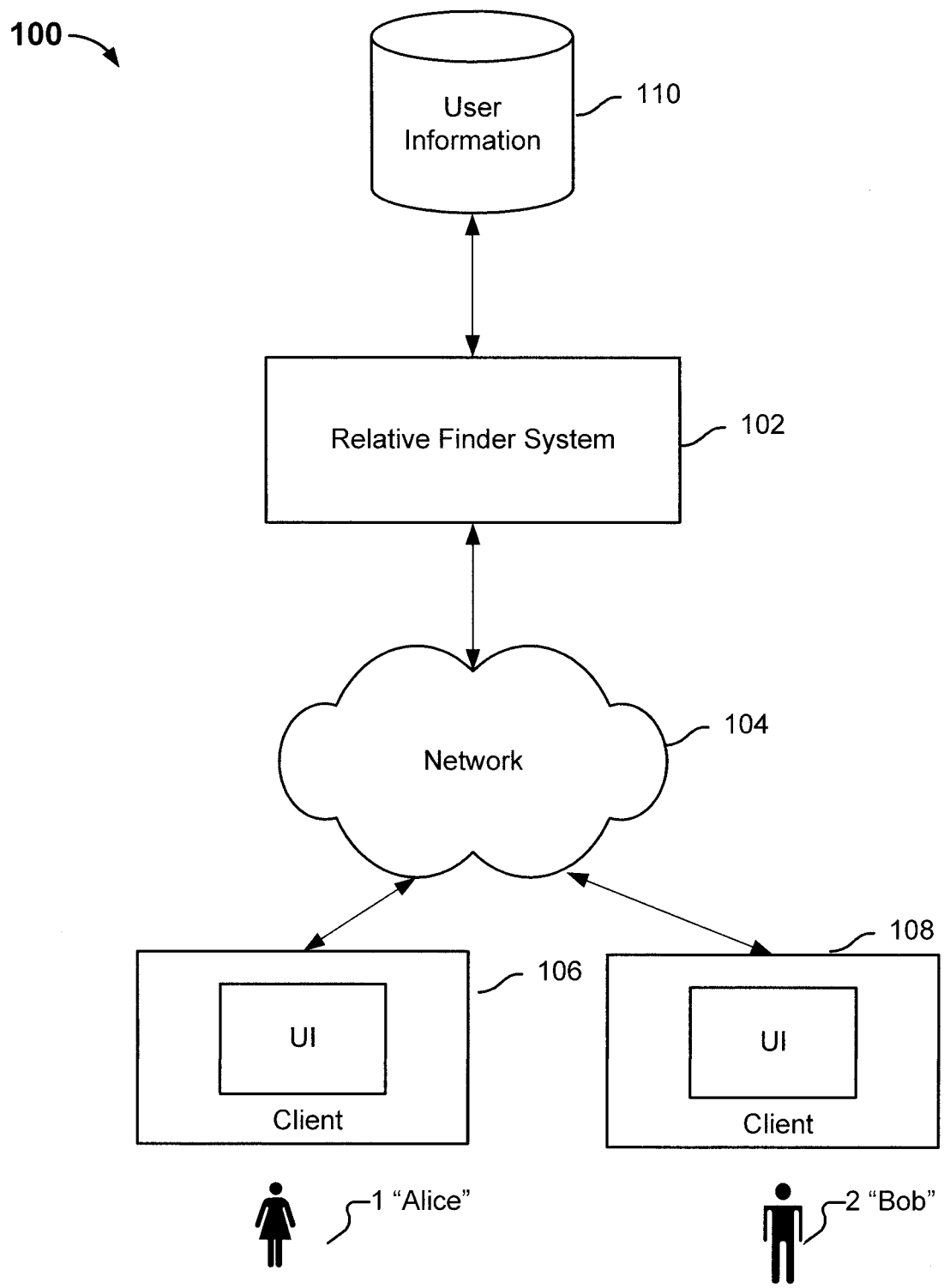
FIG. 1 is a block diagram illustrating an embodiment of a relative finding system.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Because of recombination and independent assortment of chromosomes, the autosomal DNA and X chromosome DNA (collectively referred to as recombinable DNA) from the parents is shuffled at the next generation, with small amounts of mutation. Thus, only relatives will share long stretches of genome regions where their recombinable DNA is completely or nearly identical. Such regions are referred to as "Identical by Descent" (IBD) regions because they arose from the same DNA sequences in an earlier generation. The relative finder technique described below is based at least in part on locating IBD regions in the recombinable chromosomes of individuals.

In some embodiments, locating IBD regions includes sequencing the entire genomes of the individuals and comparing the genome sequences. In some embodiments, locating IBD regions includes assaying a large number of markers that tend to vary in different individuals and comparing the markers. Examples of such markers include Single Nucleotide Polymorphisms (SNPs), which are points along the genome with two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Long stretches of DNA sequences from different individuals' genomes in which markers in the same locations are the same or at least compatible indicate that the rest of the sequences, although not assayed directly, are also likely identical.

FIG. 1 is a block diagram illustrating an embodiment of a relative finding system. In this example, relative finder system 102 may be implemented using one or more server computers having one or more processors, one or more special purpose computing appliances, or any other appropriate hardware, software, or combinations thereof. The operations of the relative finder system are described in greater detail below. In this example, various users of the system (e.g., user 1 ("Alice") and user 2 ("Bob")) access the relative finder system via a network 104 using client devices such as 106 and 108. User information (including genetic information and optionally other personal information such as family information, population group, etc.) pertaining to the users is stored in a database 110, which can be implemented on an integral storage component of the relative finder system, an attached storage device, a separate storage device accessible by the relative finder system, or a combination thereof. Many different arrangements of the physical components are possible in various embodiments. In various embodiments, the entire genome sequences or assayed DNA markers (SNPs, STRs, CNVs, etc.) are stored in the database to facilitate the relative finding process. For example, approximately 650,000 SNPs per individual's genome are assayed and stored in the database in some implementations.

System 100 shown in this example includes genetic and other additional non-genetic information for many users. By comparing the recombinable DNA information to identify IBD regions between various users, the relative finder system can identify users within the database that are relatives. Since more distant relationships (second cousins or further) are often unknown to the users themselves, the system allows the users to "opt-in" and receive notifications about the existence of relative relationships. Users are also presented with the option of connecting with their newly found relatives.

Figure 2:
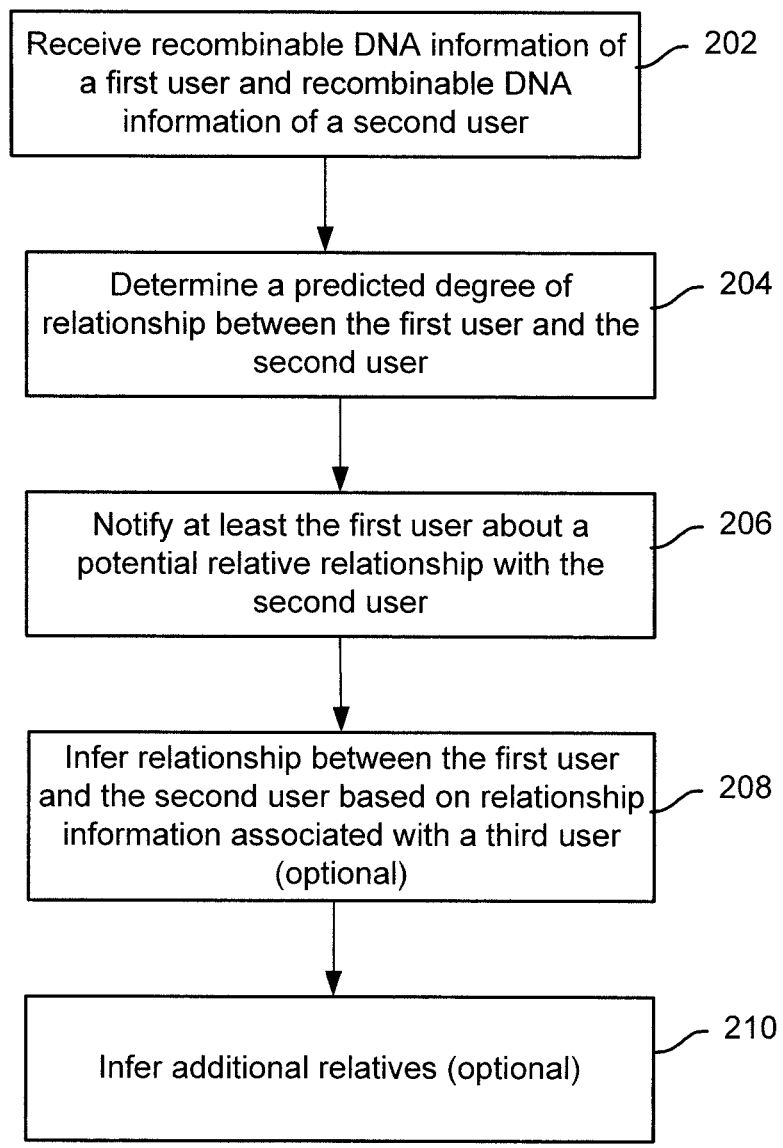
FIG. 2 is a flowchart illustrating an embodiment of a process for finding relatives in a relative finding system.

FIG. 2 is a flowchart illustrating an embodiment of a process for finding relatives in a relative finding system. Process 200 may be implemented on a relative finder system such as 100. The process may be invoked, for example, at a user's request to look for potential relatives this user may have in the database or by the system to assess the potential relationships among various users. At 202, recombinable DNA information of a first user (e.g., Alice) and of a second user (e.g., Bob) is received. In some embodiments, the information is retrieved from a database that stores recombinable DNA information of a plurality of users as well as any additional user information. For purposes of illustration, SNP information is described extensively in this and following examples. Other DNA information such as STR information and/or CNV information may be used in other embodiments.

At 204, a predicted degree of relationship between Alice and Bob is determined. In some embodiments, a range of possible relationships between the users is determined and a prediction of the most likely relationship between the users is made. In some embodiments, it is optionally determined whether the predicted degree of relationship at least meets a threshold. The threshold may be a user configurable value, a system default value, a value configured by the system's operator, or any other appropriate value. For example, Bob may select five generations as the maximum threshold, which means he is interested in discovering relatives with whom the user shares a common ancestor five generations or closer. Alternatively, the system may set a default value minimum of three generations, allowing the users to by default find relatives sharing a common ancestor at least three generations out or beyond. In some embodiments, the system, the user, or both, have the option to set a minimum threshold (e.g., two generations) and a maximum threshold (e.g., six generations) so that the user would discover relatives within a maximum number of generations, but would not be surprised by the discovery of a close relative such as a sibling who was previously unknown to the user.

At 206, Alice or Bob (or both) is notified about her/his relative relationship with the other user. In some embodiments, the system actively notifies the users by sending messages or alerts about the relationship information when it becomes available. Other notification techniques are possible, for example by displaying a list or table of users that are found to be related to the user. Depending on system settings, the potential relatives may be shown anonymously for privacy protection, or shown with visible identities to facilitate making connections. In embodiments where a threshold is set, the user is only notified if the predicted degree of relationship at least meets the threshold. In some embodiments, a user is only notified if both of the user and the potential relative have "opted in" to receive the notification. In various embodiments, the user is notified about certain personal information of the potential relative, the predicted relationship, the possible range of relationships, the amount of DNA matching, or any other appropriate information.

In some embodiments, at 208, the process optionally infers additional relationships or refines estimates of existing relationships between the users based on other relative relationship information, such as the relative relationship information the users have with a third user. For example, although Alice and Bob are only estimated to be $6^{th}$ cousins after step 204, if among Alice's relatives in the system, a third cousin, Cathy, is also a sibling of Bob's, then Alice and Bob are deemed to be third cousins because of their relative relationships to Cathy. The relative relationships with the third user may be determined based on genetic information and analysis using a process similar to 200, based on non-genetic information such as family tree supplied by one of the users, or both.

In some embodiments, the relatives of the users in the system are optionally checked to infer additional relatives at 210. For example, if Bob is identified as a third cousin of Alice's, then Bob's relatives in the system (such as children, siblings, possibly some of the parents, aunts, uncles, cousins, etc.) are also deemed to be relatives of Alice's. In some embodiments a threshold is applied to limit the relationships within a certain range. Additional notifications about these relatives are optionally generated.

Figure 3:
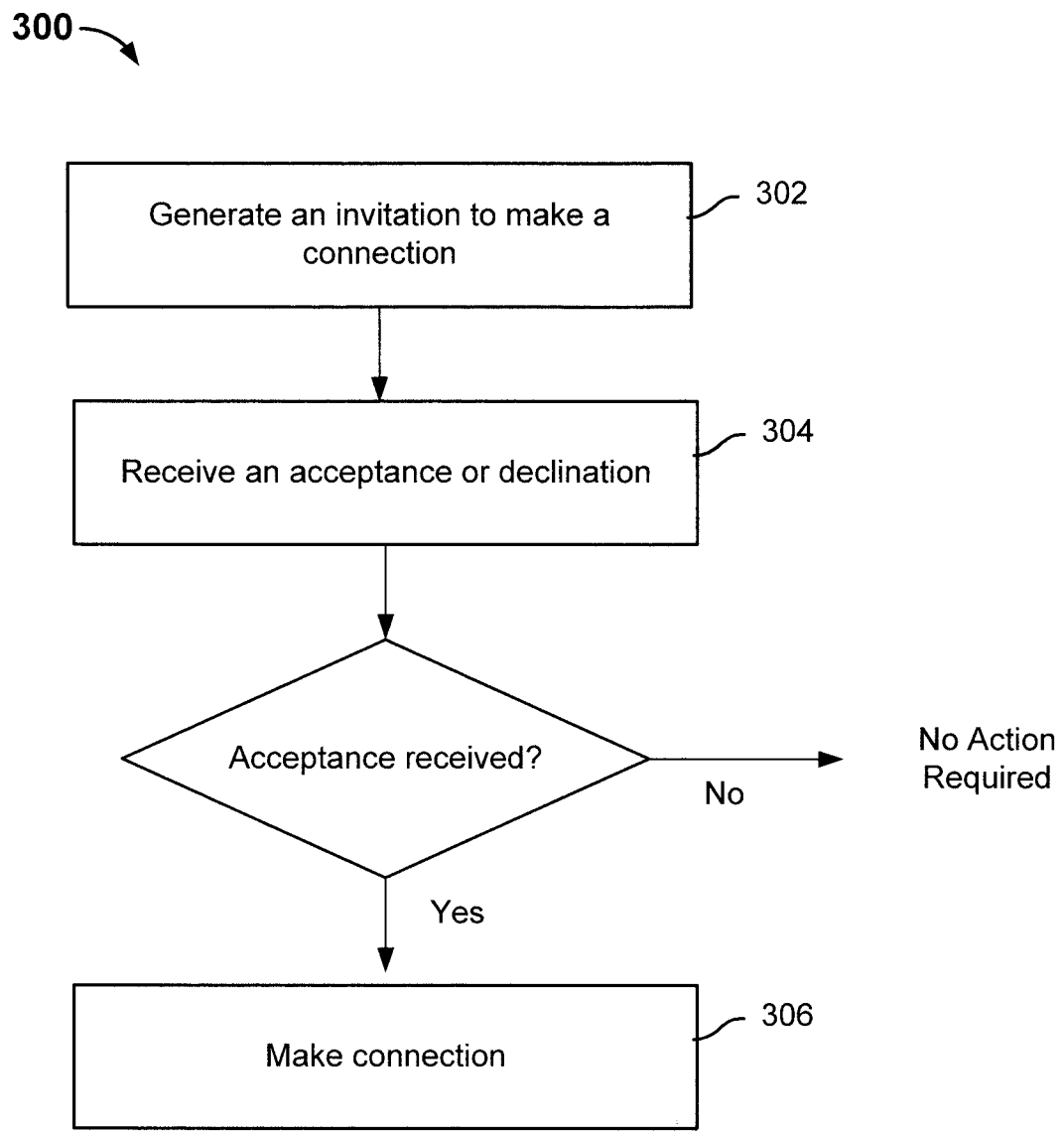
FIG. 3 is a flowchart illustrating an embodiment of a process for connecting a user with potential relatives found in the database.

Upon receiving a notification about another user who is a potential relative, the notified user is allowed to make certain choices about how to interact with the potential relative. FIG. 3 is a flowchart illustrating an embodiment of a process for connecting a user with potential relatives found in the database. The process may be implemented on a relative finder system such as 102, a client system such as 106, or a combination thereof. In this example, it is assumed that it has been determined that Alice and Bob are possibly 4th cousins and that Alice has indicated that she would like to be notified about any potential relatives within 6 generations. In this example, process 300 follows 206 of process 200, where a notification is sent to Alice, indicating that a potential relative has been identified. In some embodiments, the identity of Bob is disclosed to Alice. In some embodiments, the identity of Bob is not disclosed initially to protect Bob's privacy.

Upon receiving the notification, Alice decides that she would like to make a connection with the newly found relative. At 302, an invitation from Alice to Bob inviting Bob to make a connection is generated. In various embodiments, the invitation includes information about how Alice and Bob may be related and any personal information Alice wishes to share such as her own ancestry information. Upon receiving the invitation, Bob can accept the invitation or decline. At 304, an acceptance or a declination is received. If a declination is received, no further action is required. In some embodiments, Alice is notified that a declination has been received. If, however, an acceptance is received, at 306, a connection is made between Alice and Bob. In various embodiments, once a connection is made, the identities and any other sharable personal information (e.g., genetic information, family history, phenotype/traits, etc.) of Alice and Bob are revealed to each other and they may interact with each other. In some embodiments, the connection information is updated in the database.

In some embodiments, a user can discover many potential relatives in the database at once. Additional potential relatives are added as more users join the system and make their genetic information available for the relative finding process. FIGS. 4A-4I are screenshots illustrating user interface examples in connection with process 300. In this example, the relative finder application provides two views to the user: the discovery view and the list view.

FIG. 4A shows an interface example for the discovery view at the beginning of the process. No relative has been discovered at this point. In this example, a privacy feature is built into the relative finder application so that close relative information will only be displayed if both the user and the close relative have chosen to view close relatives. This is referred to as the "opt in" feature. The user is further presented with a selection button "show close relatives" to indicate that he/she is interested in finding out about close relatives. FIG. 4B shows a message that is displayed when the user selects "show close relatives". The message explains to the user how a close relative is defined. In this case, a close relative is defined as a first cousin or closer. In other words, the system has set a default minimum threshold of three degrees. The message further explains that unless there is already an existing connection between the user and the close relative, any newly discovered potential close relatives will not appear in the results unless the potential close relatives have also chosen to view their close relatives. The message further warns about the possibility of finding out about close relatives the user did not know he/she had. The user has the option to proceed with viewing close relatives or cancel the selection.

FIG. 4C shows the results in the discovery view. In this example, seven potential relatives are found in the database. The predicted relationship, the range of possible relationship, certain personal details a potential relative has made public, the amount of DNA a potential relative shares with the user, and the number of DNA segments the potential relative shares with the user are displayed. The user is presented with a "make contact" selection button for each potential relative.

Figure 4D:

FIG. 4D shows the results in the list view. The potential relatives are sorted according to how close the corresponding predicted relationships are to the user in icon form. The user may select an icon that corresponds to a potential relative and view his/her personal information, the predicted relationship, relationship range, and other additional information. The user can also make contact with the potential relative.

Figure 4E:
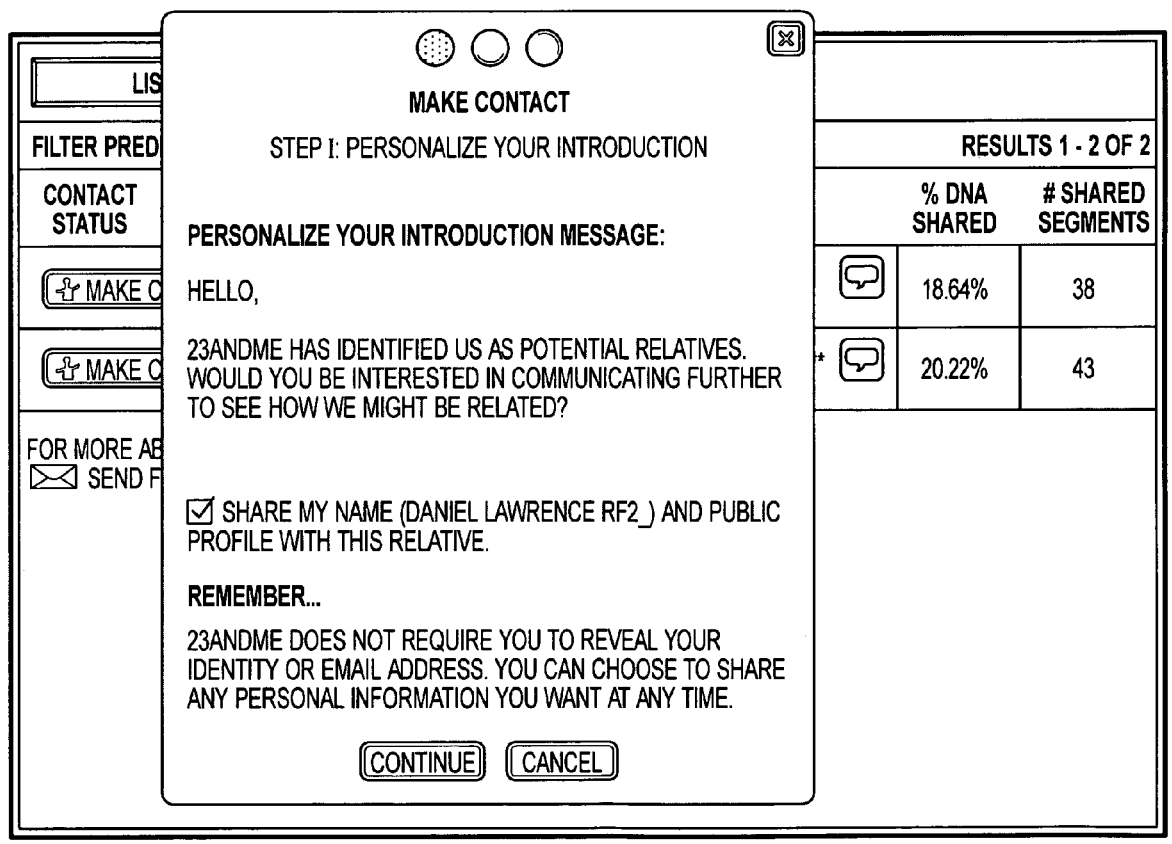
Figure 4F:
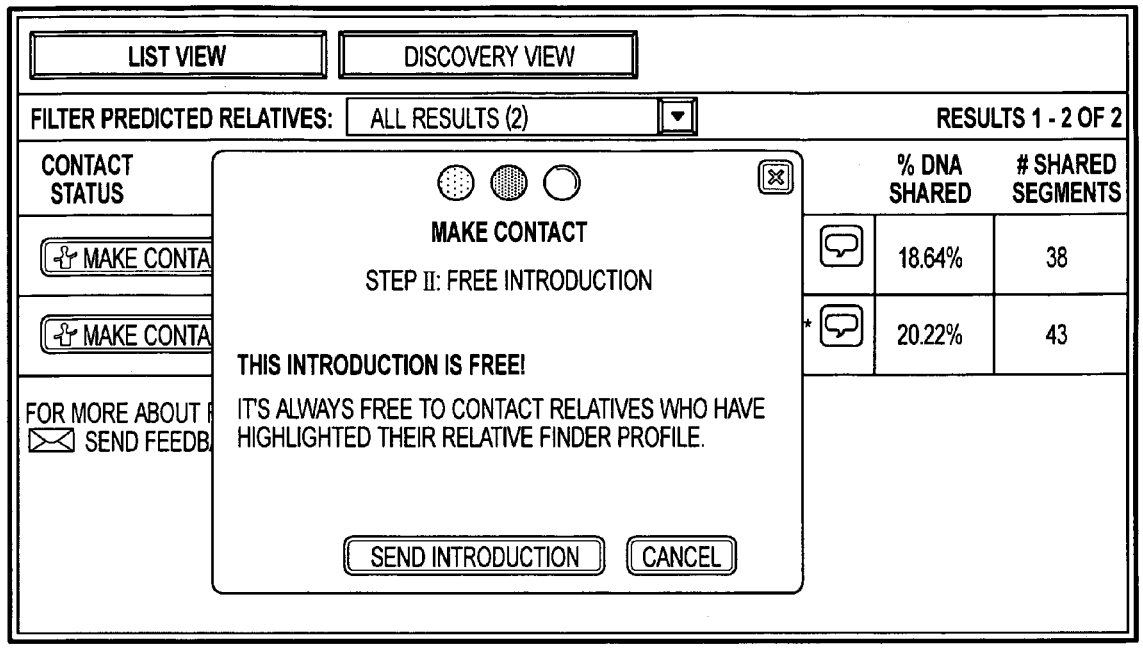
Figure 4G:
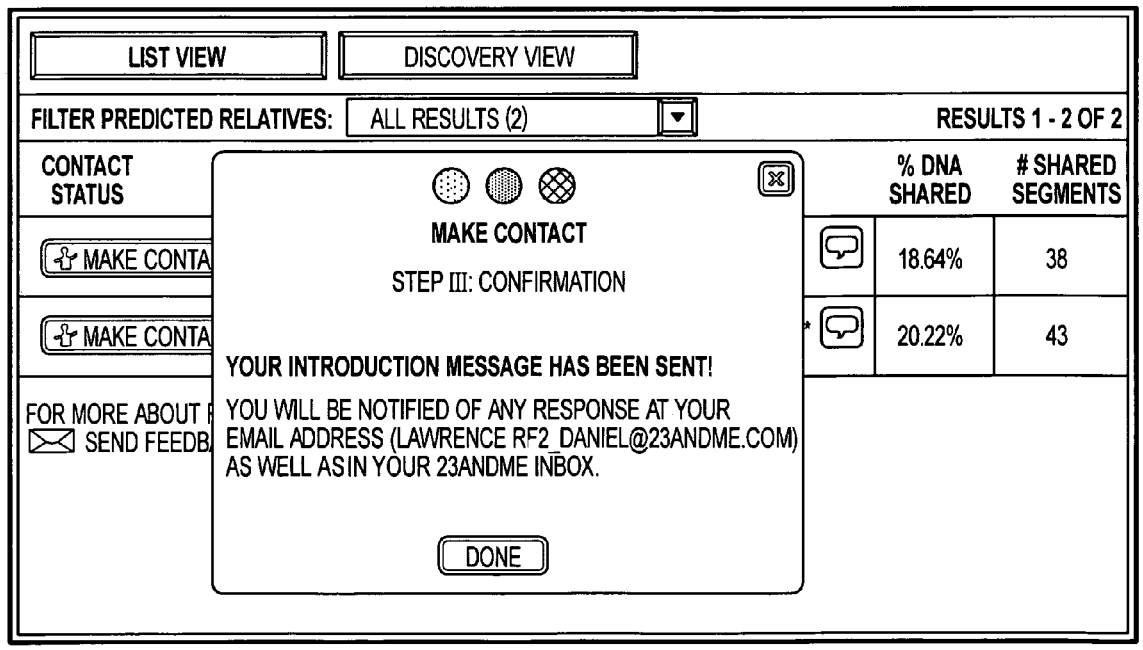

FIGS. 4E-4G show the user interface when the user selects to "make contact" with a potential relative. FIG. 4E shows the first step in making contact, where the user personalizes the introduction message and determine what information the user is willing to share with the potential relative. FIG. 4F shows an optional step in making contact, where the user is told about the cost of using the introduction service. In this case, the introduction is free. FIG. 4G shows the final step, where the introduction message is sent.

FIG. 4H shows the user interface shown to the potential relative upon receiving the introduction message. In this example, the discovery view indicates that a certain user/potential relative has requested to make a contact. The predicted relationship, personal details of the sender, and DNA sharing information are shown to the recipient. The recipient has the option to select "view message" to view the introduction message from the sender.

Figure 4I:
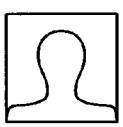

FIG. 4I shows the message as it is displayed to the recipient. In addition to the content of the message, the recipient is given the option to accept or decline the invitation to be in contact with the sender. If the recipient accepts the invitation, the recipient and the sender become connected and may view each other's information and/or interact with each other.

Many other user interfaces can be used in addition to or as alternatives of the ones shown above. For example, in some embodiments, at least some of the potential relatives are displayed in a family tree.

Determining the relationship between two users in the database is now described. In some embodiments, the determination includes comparing the DNA markers (e.g., SNPs) of two users and identifying IBD regions. The standard SNP based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g. triallelic. Other representations are possible.

In this example, A is selected to represent an allele with base A and B represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

Figure 5:
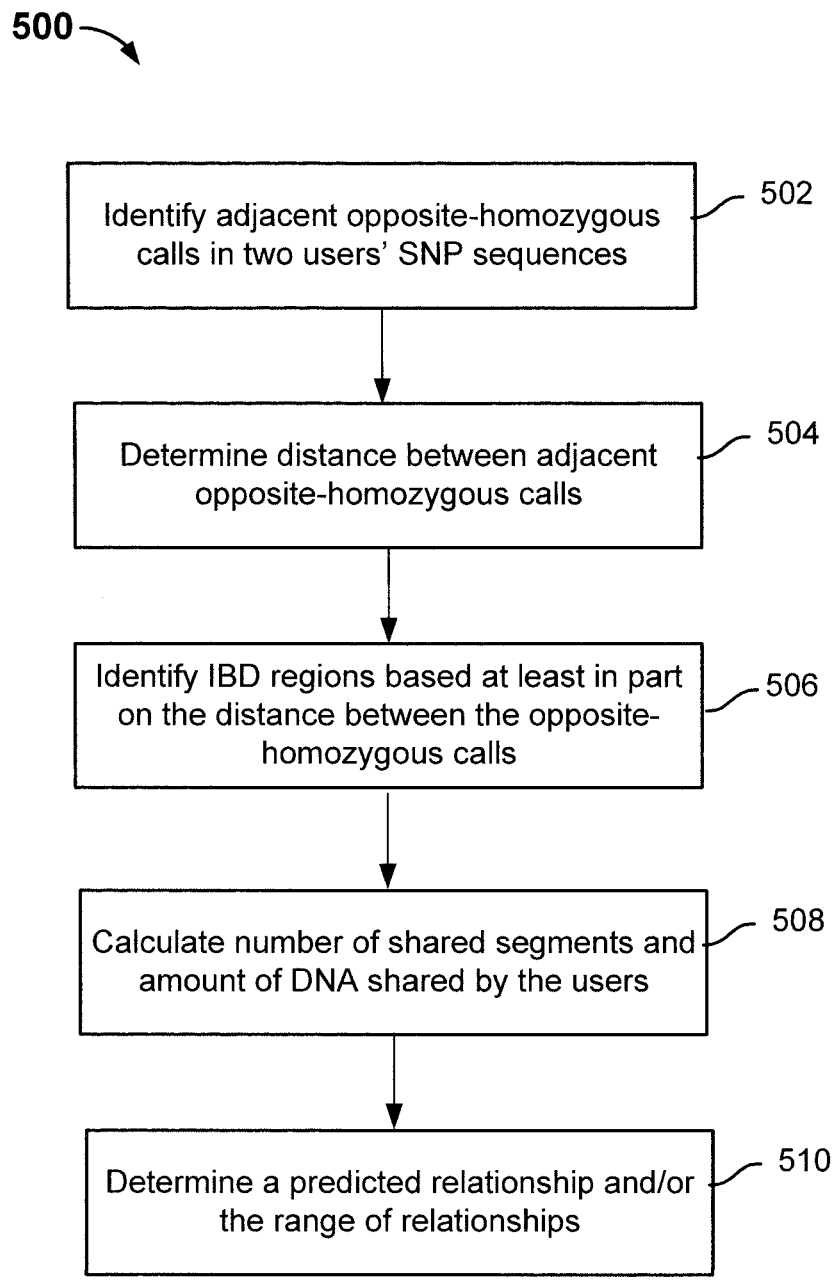
FIG. 5 is a diagram illustrating an embodiment of a process for determining the expected degree of relationship between two users.

FIG. 5 is a diagram illustrating an embodiment of a process for determining the predicted degree of relationship between two users. Process 500 may be implemented on a relative finder system such as 102 and is applicable to unphased data. At 502, consecutive opposite-homozygous calls in the users' SNPs are identified. The consecutive opposite-homozygous calls can be identified by serially comparing individual SNPs in the users' SNP sequences or in parallel using bitwise operations as described below. At 504, the distance between consecutive opposite-homozygous calls is determined. At 506, IBD regions are identified based at least in part on the distance between the opposite-homozygous calls. The distance may be physical distance measured in the number of base pairs or genetic distance accounting for the rate of recombination. For example, in some embodiments, if the genetic distance between the locations of two consecutive opposite-homozygous calls is greater than a threshold of 10 centimorgans (cM), the region between the calls is determined to be an IBD region. This step may be repeated for all the opposite-homozygous calls. A tolerance for genotyping error can be built by allowing some low rate of opposite homozygotes when calculating an IBD segment. In some embodiments, the total number of matching genotype calls is also taken into account when deciding whether the region is IBD. For example, a region may be examined where the distance between consecutive opposite homozygous calls is just below the 10 cM threshold. If a large enough number of genotype calls within that interval match exactly, the interval is deemed IBD.

Figure 6:
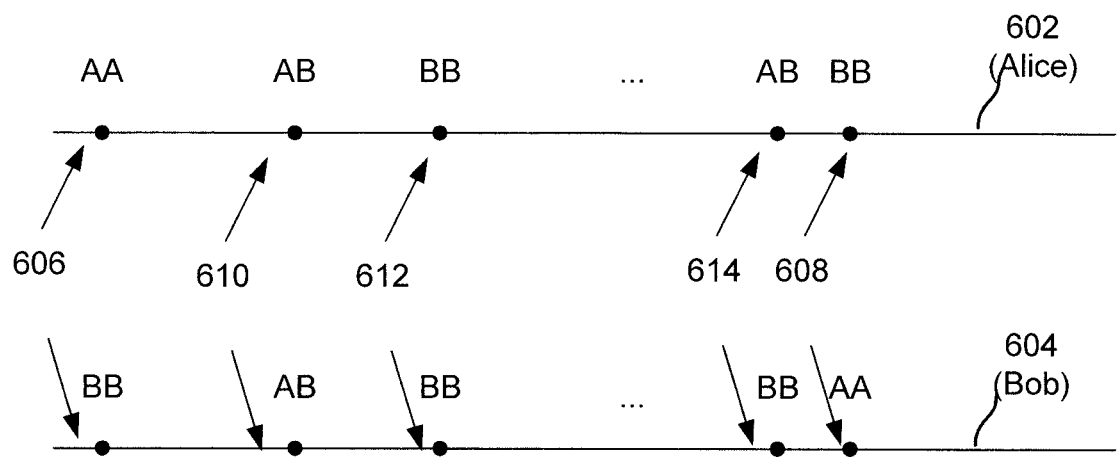
FIG. 6 is a diagram illustrating example DNA data used for IBD identification by process 500.

FIG. 6 is a diagram illustrating example DNA data used for IBD identification by process 500. 602 and 604 correspond to the SNP sequences of Alice and Bob, respectively. At location 606, the alleles of Alice and Bob are opposite-homozygotes, suggesting that the SNP at this location resides in a non-IBD region. Similarly, at location 608, the opposite-homozygotes suggest a non-IBD region. At location 610, however, both pairs of alleles are heterozygotes, suggesting that there is potential for IBD. Similarly, there is potential for IBD at location 612, where both pairs of alleles are identical homozygotes, and at location 614, where Alice's pair of alleles is heterozygous and Bob's is homozygous. If there is no other opposite-homozygote between 606 and 608 and there are a large number of compatible calls between the two locations, it is then likely that the region between 606 and 608 is an IBD region.

Returning to FIG. 5, at 508, the number of shared IBD segments and the amount of DNA shared by the two users are computed based on the IBD. In some embodiments, the longest IBD segment is also determined. In some embodiments, the amount of DNA shared includes the sum of the lengths of IBD regions and/or percentage of DNA shared. The sum is referred to as $IBD_{half}$ or half IBD because the individuals share DNA identical by descent for at least one of the homologous chromosomes. At 510, the predicted relationship between the users, the range of possible relationships, or both, is determined using the $IBD_{half}$ and number of segments, based on the distribution pattern of $IBD_{half}$ and shared segments for different types of relationships. For example, in a first degree parent/child relationship, the individuals have $IBD_{half}$ that is 100% the total length of all the autosomal chromosomes and 22 shared autosomal chromosome segments; in a second degree grandparent/grandchild relationship, the individuals have $IBD_{half}$ that is approximately half the total length of all the autosomal chromosomes and many more shared segments; in each subsequent degree of relationship, the percentage of $IBD_{half}$ of the total length is about 50% of the previous degree. Also, for more distant relationships, in each subsequent degree of relationship, the number of shared segments is approximately half of the previous number.

In various embodiments, the effects of genotyping error are accounted for and corrected. In some embodiments, certain genotyped SNPs are removed from consideration if there are a large number of Mendelian errors when comparing data from known parent/offspring trios. In some embodiments, SNPs that have a high no-call rate or otherwise failed quality control measures during the assay process are removed. In some embodiments, in an IBD segment, an occasional opposite-homozygote is allowed if there is sufficient opposite-homozygotes-free distance (e.g., at least 3 cM and 300 SNPs) surrounding the opposite-homozygote.

Figure 7:
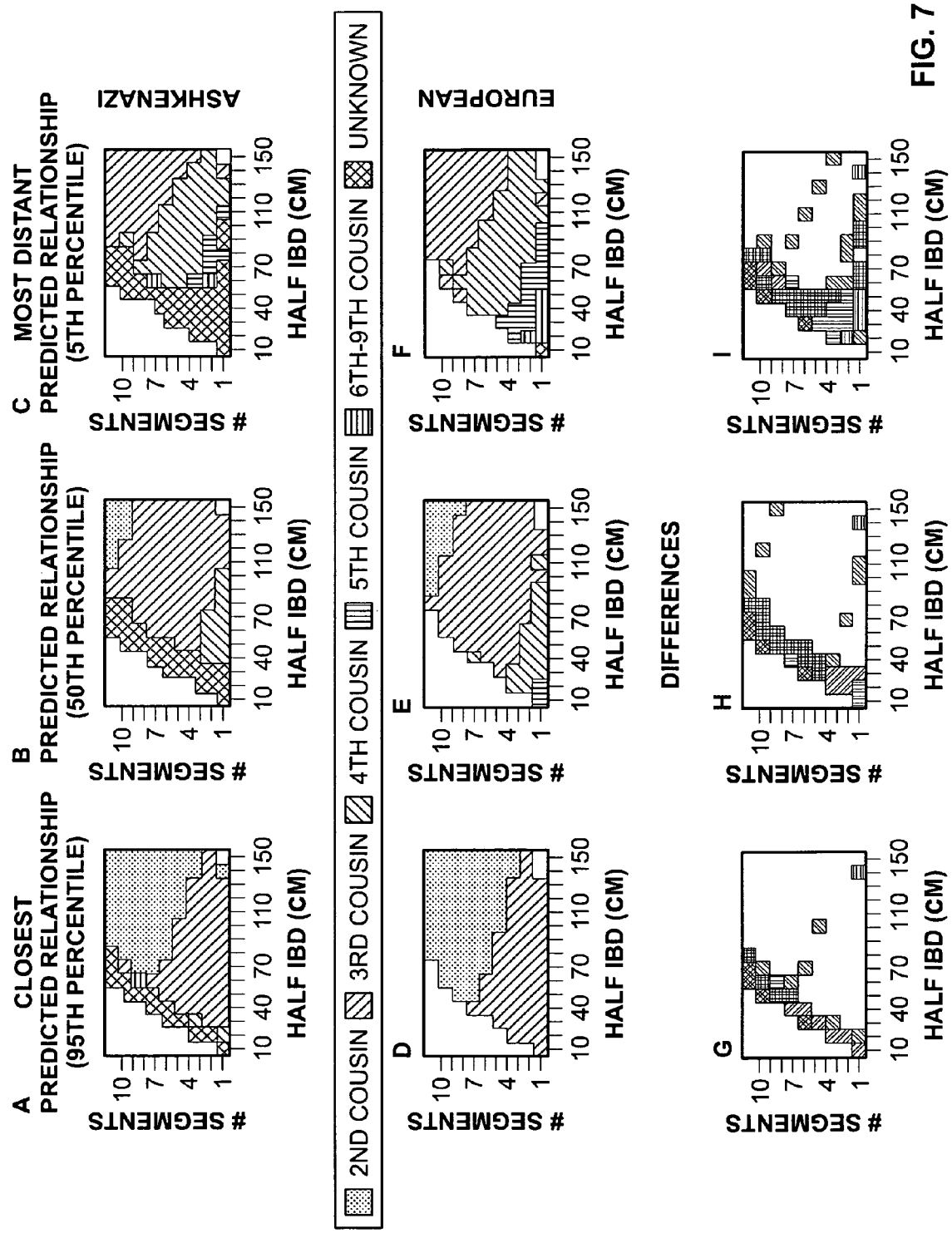
FIG. 7 shows the simulated relationship distribution patterns for different population groups according to one embodiment.

There is a statistical range of possible relationships for the same $IBD_{half}$ and shared segment number. In some embodiments, the distribution patterns are determined empirically based on survey of real populations. Different population groups may exhibit different distribution patterns. For example, the level of homozygosity within endogamous populations is found to be higher than in populations receiving gene flow from other groups. In some embodiments, the bounds of particular relationships are estimated using simulations of IBD using generated family trees. Based at least in part on the distribution patterns, the $IBD_{half}$ and shared number of segments, the degree of relationship between two individuals can be estimated. FIG. 7 shows the simulated relationship distribution patterns for different population groups according to one embodiment. In particular, Ashkenazi Jews and Europeans are two population groups surveyed. In panels A-C, for each combination of $IBD_{half}$ and the number of IBD segments in an Ashkenazi sample group, the 95%, 50% and 5% of obtained nth degree cousinships from 1 million simulated pedigrees are plotted. In panels D-F, for each combination of $IBD_{half}$ and the number of IBD segments in a European sample group, the 95%, 50% and 5% of obtained nth degree cousinships from 1 million simulated pedigrees are plotted. In panels G-I, the differences between Ashkenazi and European distant cousinship for the prior panels are represented. Each nth cousinship category is scaled by the expected number of nth degree cousins given a model of population growth. Simulations are conducted by specifying an extended pedigree and creating simulated genomes for the pedigree by simulating the mating of individuals drawn from a pool of empirical genomes. Pairs of individuals who appear to share $IBD_{half}$ that was not inherited through the specified simulated pedigree are marked as "unknown" in panels A-F. Thus, special distribution patterns can be used to find relatives of users who have indicated that they belong to certain distinctive population groups such as the Ashkenazi.

The amount of IBD sharing is used in some embodiments to identify different population groups. For example, for a given degree of relationship, since Ashkenazi tend to have much more IBD sharing than non-Ashkenazi Europeans, users may be classified as either Ashkenazi or non-Ashkenazi Europeans based on the number and pattern of IBD matches.

In some embodiments, instead of, or in addition to, determining the relationship based on the overall number of IBD segments and percent DNA shared, individual chromosomes are examined to determine the relationship. For example, X chromosome information is received in some embodiments in addition to the autosomal chromosomes. The X chromosomes of the users are also processed to identify IBD. Since one of the X chromosomes in a female user is passed on from her father without recombination, the female inherits one X chromosome from her maternal grandmother and another one from her mother. Thus, the X chromosome undergoes recombination at a slower rate compared to autosomal chromosomes and more distant relationships can be predicted using IBD found on the X chromosomes.

In some embodiments, analyses of mutations within IBD segments can be used to estimate ages of the IBD segments and refine estimates of relationships between users.

In some embodiments, the relationship determined is verified using non-DNA information. For example, the relationship may be checked against the users' family tree information, birth records, or other user information.

Figure 8:
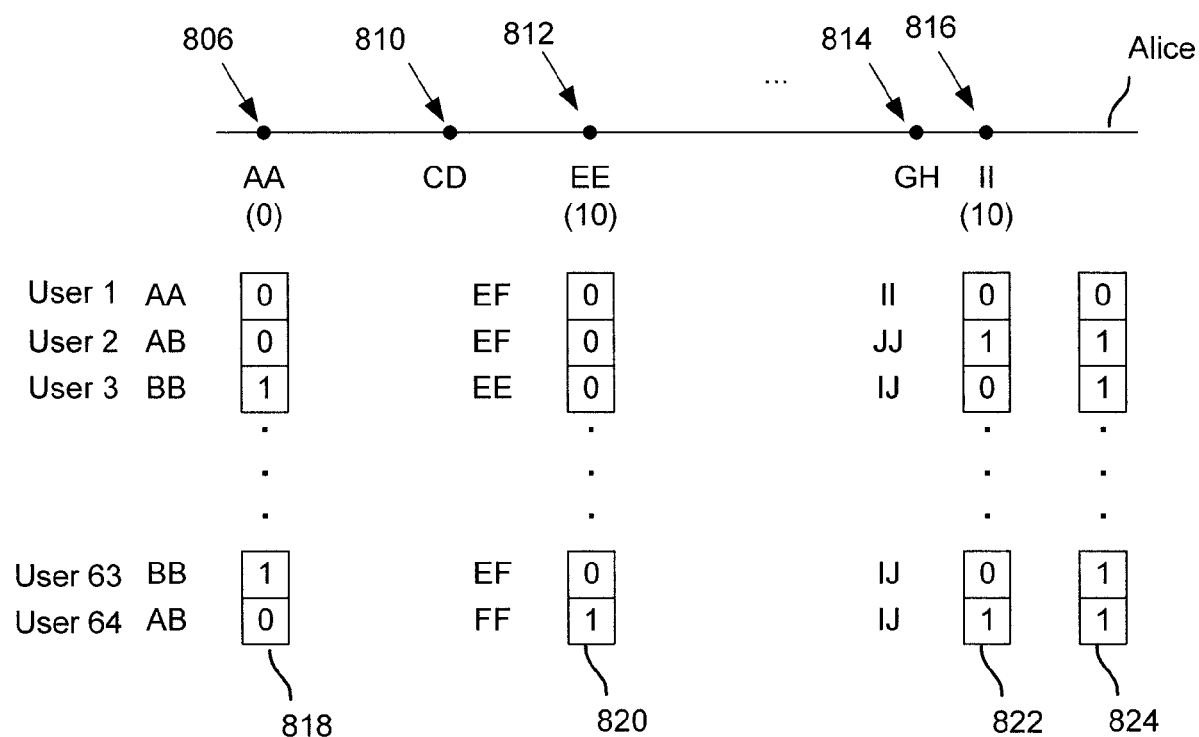
FIG. 8 is a diagram illustrating an embodiment of a highly parallel IBD identification process.

In some embodiments, the efficiency of IBD region identification is improved by comparing a user's DNA information with the DNA information of multiple other users in parallel and using bitwise operations. FIG. 8 is a diagram illustrating an embodiment of a highly parallel IBD identification process. Alice's SNP calls are compared with those of multiple other users. Alice's SNP calls are pre-processed to identify ones that are homozygous. Alice's heterozygous calls are not further processed since they always indicate that there is possibility of IBD with another user. For each SNP call in Alice's genome that is homozygous, the zygosity states in the corresponding SNP calls in the other users are encoded. In this example, compatible calls (e.g., heterozygous calls and same homozygous calls) are encoded as 0 and opposite-homozygous calls are encoded as 1. For example, for homozygous SNP call AA at location 806, opposite-homozygous calls BB are encoded as 1 and compatible calls (AA and AB) are encoded as 0; for homozygous SNP call EE at location 812, opposite-homozygous calls FF are encoded as 1 and compatible calls (EE and EF) are encoded as 0, etc. The encoded representations are stored in arrays such as 818, 820, and 824. In some embodiments, the length of the array is the same as the word length of the processor to achieve greater processing efficiency. For example, in a 64-bit processing system, the array length is set to 64 and the zygosity of 64 users' SNP calls are encoded and stored in the array.

A bitwise operation is performed on the encoded arrays to determine whether a section of DNA such as the section between locations 806 and 810 includes opposite-homozygous calls. In this example, a bitwise OR operation is performed to generate a result array 824. Any user with no opposite-homozygous calls between beginning location 806 and ending location 816 results in an entry value of 0 in array 824. The corresponding DNA segment, therefore, is deemed as an IBD region for such user and Alice. In contrast, users with opposite-homozygotes result in corresponding entry values of 1 in array 824 and they are deemed not to share IBD with Alice in this region. In the example shown, user 1 shares IBD with Alice while other users do not.

In some embodiments, phased data is used instead of unphased data. These data can come directly from assays that produce phased data, or from statistical processing of unphased data. IBD regions are determined by matching the SNP sequences between users. In some embodiments, sequences of SNPs are stored in dictionaries using a hash-table data structure for the ease of comparison. FIG. 9 is a diagram illustrating an example in which phased data is compared to identify IBD. The sequences are split along pre-defined intervals into non-overlapping words. Other embodiments may use overlapping words. Although a preset length of 3 is used for purposes of illustration in the example shown, many implementations may use words of longer lengths (e.g. 100). Also, the length does not have to be the same for every location. In FIG. 9, in Alice's chromosome pair 1, chromosome 902 is represented by words AGT, CTG, CAA, . . . and chromosome 904 is represented by CGA, CAG, TCA, . . . . At each location, the words are stored in a hash table that includes information about a plurality of users to enable constant retrieval of which users carry matching haplotypes. Similar hash tables are constructed for other sequences starting at other locations. To determine whether Bob's chromosome pair 1 shares any IBD with Alice's, Bob's sequences are processed into words at the same locations as Alice's. Thus, Bob's chromosome 906 yields CAT, GAC, CCG, . . . and chromosome 908 yields AAT, CTG, CAA, . . . . Every word from Bob's chromosomes is then looked up in the corresponding hash table to check whether any other users have the same word at that location in their genomes. In the example shown, the second and third words of chromosome 908 match second and third words of Alice's chromosome 902. This indicates that SNP sequence CTGCAA is present in both chromosomes and suggests the possibility of IBD sharing. If enough matching words are present in close proximity to each other, the region would be deemed IBD.

In some embodiments, relative relationships found using the techniques described above are used to infer characteristics about the users that are related to each other. In some embodiments, the inferred characteristic is based on non-genetic information pertaining to the related users. For example, if a user is found to have a number of relatives that belong to a particular population group, then an inference is made that the user may also belong to the same population group. In some embodiments, genetic information is used to infer characteristics, in particular characteristics specific to shared IBD segments of the related users. Assume, for example, that Alice has sequenced her entire genome but her relatives in the system have only genotyped SNP data. If Alice's genome sequence indicates that she may have inherited a disease gene, then, with Alice's permission, Alice's relatives who have shared IBD with Alice in the same region that includes the disease gene may be notified that they are at risk for the same disease.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for determining a relative relationship of people who share a common ancestor within a threshold number of generations, comprising:
 obtaining recombinable deoxyribonucleic acid (DNA) sequence information of a first user and recombinable sequence DNA information of a second user; wherein the recombinable DNA sequence information of the first user and the recombinable DNA sequence information of the second user are stored in a database comprising recombinable DNA sequence information of a plurality of users;
 determining, using one or more computer processors, based at least in part on a comparison of the recombinable DNA sequence information of the first user and the recombinable DNA sequence information of the second user, a predicted degree of relative relationship that corresponds to a number of generations within which the first user and the second user share a common ancestor; and
 notifying at least the first user about the relative relationship with the second user.

2. The method of claim 1, wherein the threshold number of generations is preconfigured; and determining the predicted degree of relationship includes determining whether the number of generations within which the first user and the second user share a common ancestor at least meets the threshold number of generations.

3. The method of claim 1, wherein the recombinable DNA sequence information includes autosomal DNA sequence information.

4. The method of claim 1, wherein the recombinable DNA sequence information includes X chromosome DNA sequence information.

5. The method of claim 1, wherein the predicted degree of relative relationship indicates that the first user and the second user share a common ancestor at least three generations out or beyond.

6. The method of claim 1, further comprising sending, via a user interface, an invitation to connect from said at least one user to the other user.

7. The method of claim 1, wherein:
determining the predicted degree of relationship between the first user and the second user includes identifying one or more Inheritance By Descent (IBD) regions in which a portion of recombinable DNA sequence of the first user and a portion of recombinable DNA sequence of the second user arose from same DNA sequence of an ancestor;
the predicted degree of relationship depends at least in part on an amount of DNA sequence information of the IBD regions;
the amount of DNA sequence information of the IBD regions includes a sum of the lengths of IBD regions, percentage of DNA shared in the IBD regions, or both; and
a greater amount of DNA sequence information of the IBD regions indicates a closer predicted degree of relationship.

8. The method of claim 1, wherein determining a predicted degree of relationship between the first user and the second user includes using a distribution pattern that indicates a distribution of amounts of DNA shared by individuals and corresponding relative relationships to determine the predicted relative relationship or a range of relative relationships.

9. The method of claim 8, wherein the distribution pattern is an initial distribution pattern, and the initial distribution pattern is adjusted based on a population group to which at least one of the users belongs, and the population group is associated with a corresponding distribution pattern that is different from the initial distribution pattern.

10. The method of claim 1, wherein the DNA sequence information includes single-nucleotide polymorphism (SNP) information.

11. The method of claim 10, wherein the SNP information includes unphased genotype information.

12. The method of claim 7, wherein identifying one or more IBD regions includes:
identifying consecutive opposite-homozygous calls in a SNP sequence of the first user and in a SNP sequence of the second user, wherein the first user and the second user have opposite-homozygous calls at a given SNP location where the first user and the second user do not share an allele;
determining, based at least in part on a distance between the consecutive opposite-homozygous calls, whether a region between the opposite-homozygous calls is an IBD region.

13. The method of claim 12, wherein the distance is a genetic distance.

14. The method of claim 10, wherein the SNP sequence information includes phased genotype information.

15. The method of claim 14, further comprising:
storing a first plurality of SNP sequence words that corresponds to SNP sequence information of the first user in one or more hash tables, wherein a SNP sequence word includes encoded SNP sequence information stored in an array;
and wherein the comparison of the recombinable DNA sequence information of the first user and the recombinable DNA sequence information of the second user includes determining whether one or more consecutive SNP sequence words in a second plurality of SNP sequence words of the second user matches one or more consecutive SNP sequence words stored in said one or more hash tables.

16. The method of claim 1, wherein the DNA sequence information comprises genotype information, and the method further comprises correcting genotyping error in the DNA sequence information.

17. The method of claim 1, wherein the relative relationship is one of a range of possible relative relationships between the first user and the second user, and wherein notifying includes sending an indication of the range of possible relative relationships between the first user and the second user.

18. The method of claim 1, wherein notifying includes sending, via a network, an indication of a predicted relationship.

19. The method of claim 2, wherein the threshold number of generations corresponds to is a minimum predicted degree of relationship.

20. The method of claim 1, further comprising providing the second user with an option to be contacted by potential relatives, and wherein notifying is performed only if the second user has agreed to be contacted by potential relatives.

21. The method of claim 1, wherein:
the first user has a known characteristic; and
the method further comprises inferring that the second user has the same characteristic given that the first user and the second user are related and the known characteristic is likely shared by people who are related.

22. The method of claim 7, wherein:
the first user has a known characteristic that is a genotype or a phenotype associated with one or more genes in the one or more IBD regions; and
the method further comprises inferring that the second user has the same characteristic given that the first user and the second user share said one or more IBD regions.

23. The method of claim 22, wherein the characteristic is an inherited disease.

24. The method of claim 1, further comprising determining a relative relationship of a third user with respect to the first user, a relative relationship of the third user with respect to the second user, or both;
inferring or refining a relative relationship between the first user and the second user given the relative relationship information of a third user with respect to the first user, the relative relationship of the third user with respect to the second user, or both, and given the predicted degree of relative relationship between the first user and the second user.

25. The method of claim 1, further comprising:
determining a relative relationship of a third user with respect to the second user;
inferring an additional relative relationship or refining an existing predicted relative relationship between the first user and the third user, given the predicted degree of relative relationship between the first user and the second user, and given the relative relationship of the third user with respect to the second user.

26. A system for determining a relative relationship of people who share a common ancestor within a threshold number of generations, comprising:
one or more processors configured to:
receive recombinable deoxyribonucleic acid (DNA) information of a first user and recombinable DNA sequence information of a second user; wherein the recombinable DNA sequence information of the first user and the recombinable DNA sequence information of the second user are stored in a database comprising recombinable DNA sequence information of a plurality of users;

determine, based at least in part on a comparison of the recombinable DNA sequence information of the first user and the recombinable DNA sequence information of the second user, a predicted degree of relationship that corresponds to a number of generations within which the first user and the second user share a common ancestor; and notify at least the first user about a relative relationship with the second user; and a memory coupled to at least some of the one or more processors, configured to provide the processors with instructions.

27. A computer program product for determining a relative relationship of people who share a common ancestor within a threshold number of generations, the computer program product being embodied in a tangible computer readable storage medium and comprising computer instructions for:

receiving recombinable deoxyribonucleic acid (DNA) sequence information of a first user and recombinable DNA sequence information of a second user; wherein the recombinable DNA sequence information of the first user and the recombinable DNA sequence information of the second user are stored in a database comprising recombinable DNA sequence information of a plurality of users;

determining, based at least in part on a comparison of the recombinable DNA sequence information of the first user and the recombinable DNA sequence information of the second user, a predicted degree of relationship that corresponds to a number of generations within which the first user and the second user share a common ancestor; and notifying at least the first user about a relative relationship with the second user.

28. The system of claim 26, wherein the recombinable DNA sequence information includes autosomal DNA sequence information.

29. The system of claim 26, wherein the recombinable DNA sequence information includes X chromosome DNA sequence information.

30. The system of claim 26, wherein the one or more processors are further configured to send an invitation to connect from said at least one user to the other user.

31. The system of claim 26, wherein to determine the predicted degree of relationship between the first user and the second user includes to identify one or more Inheritance By Descent (IBD) regions in which a portion of recombinable DNA sequence of the first user and a portion of recombinable DNA sequence of the second user arose from same DNA sequence of an ancestor;

the predicted degree of relationship depends at least in part on an amount of DNA sequence information of the IBD regions;

the amount of DNA sequence information of the IBD regions includes a sum of the lengths of IBD regions, percentage of DNA shared in the IBD regions, or both; and a greater amount of DNA sequence information of the IBD regions indicates a closer predicted degree of relationship.

32. The system of claim 26, wherein the relative relationship is one of a range of possible relative relationships between the first user and the second user, and wherein to notify includes to send an indication of the range of possible relative relationships between the first user and the second user.

33. The system of claim 26, wherein the one or more processors are further configured to provide the second user with an option to be contacted by potential relatives, and wherein notifying is performed only if the second user has agreed to be contacted by potential relatives.

34. The computer program product of claim 27, wherein the recombinable DNA sequence information includes autosomal DNA sequence information.

35. The computer program product of claim 27, wherein the recombinable DNA sequence information includes X chromosome DNA sequence information.

36. The computer program product of claim 27, further comprising computer instructions for sending an invitation to connect from said at least one user to the other user.

37. The computer program product of claim 27, wherein determining the predicted degree of relationship between the first user and the second user includes identifying one or more Inheritance By Descent (IBD) regions in which a portion of recombinable DNA sequence of the first user and a portion of recombinable DNA sequence of the second user arose from same DNA sequence of an ancestor;

the predicted degree of relationship depends at least in part on an amount of DNA sequence information of the IBD regions;

the amount of DNA sequence information of the IBD regions includes a sum of the lengths of IBD regions, percentage of DNA shared in the IBD regions, or both; and a greater amount of DNA sequence information of the IBD regions indicates a closer predicted degree of relationship.

38. The computer program product of claim 27, wherein the relative relationship is one of a range of possible relative relationships between the first user and the second user, and wherein notifying includes sending an indication of the range of possible relative relationships between the first user and the second user.

39. The computer program product of claim 27, further comprising computer instructions for providing the second user with an option to be contacted by potential relatives, and wherein notifying is performed only if the second user has agreed to be contacted by potential relatives.

* * * * *